(12) United States Patent
Al-Najjar

(10) Patent No.: US 7,320,706 B2
(45) Date of Patent: Jan. 22, 2008

(54) ARTIFICIAL HEART

(76) Inventor: Azad Al-Najjar, Skiljebovägen 9, SE-723 41 Västerås (SE)

( * ) Notice: Subject to any disclaimer, the term of this patent is extended or adjusted under 35 U.S.C. 154(b) by 503 days.

(21) Appl. No.: 10/706,790

(22) Filed: Nov. 12, 2003

(65) Prior Publication Data

US 2006/0173538 A1 Aug. 3, 2006

Related U.S. Application Data

(63) Continuation of application No. PCT/SE02/00689, filed on Apr. 8, 2002.

(30) Foreign Application Priority Data

Apr. 10, 2001 (SE) .................................... 0101259

(51) Int. Cl.
*A61M 1/12* (2006.01)
(52) U.S. Cl. ....................... 623/3.19; 623/3.2
(58) Field of Classification Search ................. 600/16, 600/17; 623/3.11, 3.17, 3.2, 3.16, 3.18, 3.19, 623/3.21–3.25, 3.28, FOR. 102
See application file for complete search history.

(56) References Cited

U.S. PATENT DOCUMENTS

| | | | |
|---|---|---|---|
| 4,809,676 A | 3/1989 | Freeman | |
| 5,135,539 A | 8/1992 | Carpentier | |
| 5,139,517 A | 8/1992 | Corral | |
| 5,676,162 A * | 10/1997 | Larson et al. | 128/899 |
| 6,099,460 A | 8/2000 | Denker | |
| 6,123,724 A | 9/2000 | Denker | |

FOREIGN PATENT DOCUMENTS

| | | | |
|---|---|---|---|
| FR | 2 485 928 | * | 1/1982 |
| WO | WO 95/09660 | | 4/1995 |

* cited by examiner

*Primary Examiner*—David H. Willse
(74) *Attorney, Agent, or Firm*—Gauthier & Connors LLP

(57) ABSTRACT

The present invention relates to a heart prosthesis/artificial heart comprising a series of drawing and pressing devices. The prosthesis/artificial heart is to be implanted in a patient to replace the pumping activity of a heart. The heart comprises at least two compartments (5, 6, 12, 13, 25, 26, 27, 28), substantially surrounded by a rigid-wall provided house (2, 3, 31). The house contains a number of drawing and/or pressing devices (10, 48, 50), which are partly fixedly attached to the rigid-wall provided house (2, 3, 31) and are partly fixedly attached to a flexible, elastic wall layer (7, 30) arranged in a respective compartment. The drawing and/or pressing devices (10, 48, 50) are arranged to draw the elastic wall layers (7, 30) towards the rigid-wall provided house (2, 3, 31) for filling the compartments (12, 13, 27, 28).

7 Claims, 12 Drawing Sheets

ARTIFICIAL HEART

PRIORITY INFORMATION

This application is a continuation of PCT Application No. PCT/SE02/00689, filed on Apr. 8, 2002, which claims priority to Swedish Patent Application No. 0101259-0, filed Apr. 10, 2001.

TECHNICAL FIELD

The present invention relates to an artificial heart comprising a series of towing and pressing means and intended to be implanted in a patient to replace the pumping activity of a heart.

The object of the present invention is to obtain an artificial heart to be implanted into a patient to replace whole of or part of the activity of a heart.

BACKGROUND OF THE INVENTION

The last years there has been an increased demand within cardiology for an efficient heart prosthesis.

Heart diseases and often in combination with circulatory diseases give rise to a serious threat against the patient's life.

Heart failure, as a result of a longterm weakness of the function of the heart, is a very serious condition and will sooner or later lead to death.

Access to healthy donator hearts is also very restricted and a patient may have to wait for several years for a suitable heart to be presented for implantation.

For these reasons it is of great importance to find and develop an artificial heart or rather an apparatus which can offer a continuous, harmless, comfortable, and reliable substitute for a weak, failing heart.

For many years a number of artificial heart prostheses have been introduced. However, these show a number of deficiencies and drawbacks, such as lack of implantability, lack of physiological pliability, lack of longterm use as well as lack of pliability with regard to beat-volume.

U.S. Pat. No. 5,139,517 shows an artificial heart which is hydraulically operated by activation from a pacemaker.

U.S. Pat. No. 5,135,539 shows a heart prosthesis working with an electromechanical device in the form of a hydraulic micropump.

FR-A-2,710,847 shows an artificial heart having two different sacks and being operated by hydraulic oil.

U.S. Pat. No. 4,809,676 shows a device to be implanted around aorta and which is controlled by a series of electromagnets placed opposite each other. When the electromagnets are activated aorta will be compressed between these so that a pumping movement is obtained.

WO 99/55399 shows an electromagnetically controlled heart assistance technology where a number of electromagnets are placed on the outside of the living heart, which means that one has an electromagnetically supported heart.

U.S. Pat. No. 6,099,460 shows an artificial heart having flexible outer walls which are influenced by electromagnets, partly applied on the outer walls of the flexible walls, partly applied on the inside of the heart.

U.S. Pat. No. 6,123,724 shows a construction to influence a heart by means of electromagnetic coils attached to the ribs and permanent magnets placed adjacent the electromagnetic coils. It is hereby a matter of supporting function when the normal pacing of a heart does not function.

U.S. Pat. No. 6,197,055 relates to a single chamber prosthesis having a movable wall which obtains pumping by being turned from one side to the other.

U.S. Pat. No. 5,383,840 relates to a heart supporting construction having a compression pad to surround a common heart by means of which compression pad the pumping of the heart is obtained.

None of these references discloses a rigid-wall provided prosthesis having inner flexible compartments.

SUMMARY OF THE INVENTION

It has now surprisingly been shown possible to be able to solve these above-mentioned deficiencies by means of the present invention, which is characterized in that it comprises at least two compartments, substantially surrounded by rigid-wall provided house containing a number of electromagnets, which are partly fixedly attached to said rigid-wall provided house, partly fixedly attached to a flexible, elastic wall layer arranged in the respective compartment, whereby the electromagnets are arranged to draw said elastic wall layer towards said rigid-wall provided house for filling said compartments.

BRIEF DESCRIPTION OF THE DRAWINGS

The present invention will now be described more in detail in the following with reference to the accompanying drawing, wherein.

DESCRIPTION OF THE PRESENT INVENTION

Figure 1:
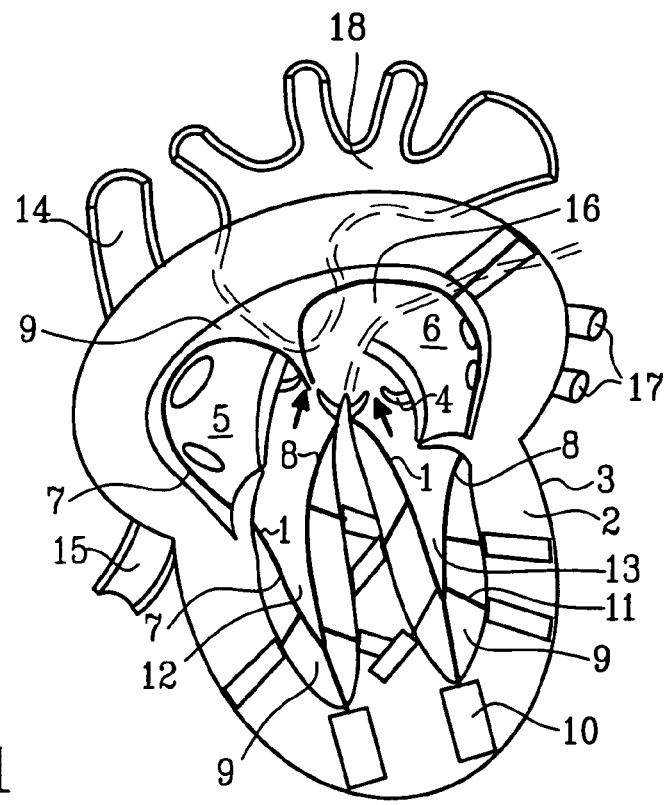
FIG. 1 shows a first embodiment of the present invention in a ventricular systole phase.
Figure 2:
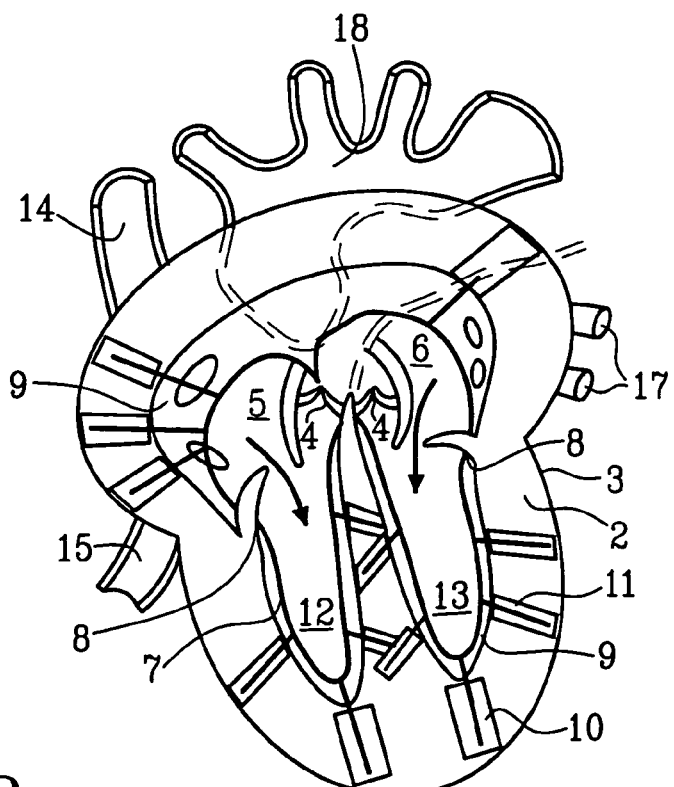
FIG. 2 shows the embodiment of FIG. 1 in an atrial systole phase.

The actual function of the present invention is clearly apparent from the figures shown, as well as from the following disclosure of the natural circulation system.

The heart is surrounded by the heart sac, the pericardium, whereby the heart contains four cavities, right atrium, right ventricle, left atrium and left ventricle. The atriums are divided by the thin walled atrial septum, while the ventricles are separated by a thick walled ventricular septum. In the right atrium the two vena cavas, vena cava superior and vena cava inferior, end. From the right atrium the blood flows through the tricuspidalisostium with its valve equipment (valvula tricuspidalis) to the right ventricle from where it is then pumped via the pulmonalisostium and its valves (valvula pulmonalis) to the pulmonary artery (arteria pulmonalis).

The oxygenated blood from the lungs flows via the four pulmonary veins (venae pulmonalis) to the left atrium and then further to the left ventricle through the mitralis valve (valvula mitralis). The left ventricle is ellipsoidal in shape and not so trabecular as the right ventricle. Its myocardium, muscle wall, is 3-5 times thicker than the one of the right ventricle, which is due to the higher pressure work carried out in the left ventricle. It should be noted that the left ventricle is dorsally placed, while the right ventricle is ventrally placed. From the left ventricle the blood is pumped out into the large body artery, the aorta.

The task of the heart is keep the blood circulating in the body. From a physiological point of view, it consists of two pumps connected in series, the right heart and the left heart. The atriums operate as reservoirs to the ventricles and facilitate a rapid filling of these during the filling phase of the heart, diastole. During the ejection phase, systole, the blood is driven with a high speed out into the aorta and arteria pulmonalis.

During rest the heart pumps 4-5 liters per minute. The blood pressure in the right ventricle during systolic phase is 15-30 mm Hg while it is 120-150 mm Hg during systolic phase in the left ventricle.

The heart cycle is normally divided into two phases, diastole—the filling of the ventricles—and systole—the emptying of the ventricles. Diastole, in turn, can be divided into three parts, viz. a first third part, a second third part and a last third part, whereby the atriums during the last third part are contracted (atrial systole).

| Phase 1 diastole | | | Phase 2 systole |
|---|---|---|---|
| First third part Rapid filling | Second third part | Last third part Atrial contraction | Contraction of the ventricles |

In the present description the heart cycle is divided into three phases to be able to compare the natural cycle with cycle/function of the artificial heart. Hereby the three phases are diastole, atrial systole and ventricular systole

| Phase 1 diastole | Phase 2 atrial systole | Phase 3 ventricular systole |
|---|---|---|

The three phases of the heart rhythm are:

Diastole: During the first phase of the heart rhythm, diastole, the heart is filled with blood, and during the greater part of diastole the blood flows in the atriums and through the valves between the atriums and the ventricles.

Atrial systole: The subsequent phase is called atrial systole when the atriums contract so that the remaining blood is pressed into the ventricles.

Ventricular systole: At the end of the atrial systole and after a short delay the ventricles start to contract, whereby the pressure therein is higher than in the atriums, and the valves between the atriums and the ventricles are closed and the blood is forced out of the heart and into the pulmonary artery, arteria pulmonalis, and into the large body artery, aorta.

The natural heart contraction is released by electrical signals (action potentials) which derive from the sinoatrial bundle, which is a small collection of cells, which depolarize themselves so that action potentials are released. The sinoatrial bundle is present in the right atrium adjacent the mouth of vena cava superior. When action potentials have been created in the sinoatrial bundle, these will spread through the whole heart in a system of specialized muscle cells which lead these impulses through the heart and release a contraction. The sinoatrial bundle is thereby the natural pace-maker of the heart (frequency determinator). Generally, the sinoatrial bundle provides 60-70 impulses per minute.

The most known idea concerning pumping of blood from the heart has been what is called Asqueezing motion®, i.e., one has regarded the pumping e.g., from the left ventricle as a contraction of the volume of the ventricle by a contraction of the walls of the ventricle. This hypothesis has now, however, been modified.

In 1932 Hamilton & Rompf proved the importance of the long axis contraction of the left ventricle. Their principle of the pumping of the heart has then formed the basis for a larger research work during the later years.

Figure 13:
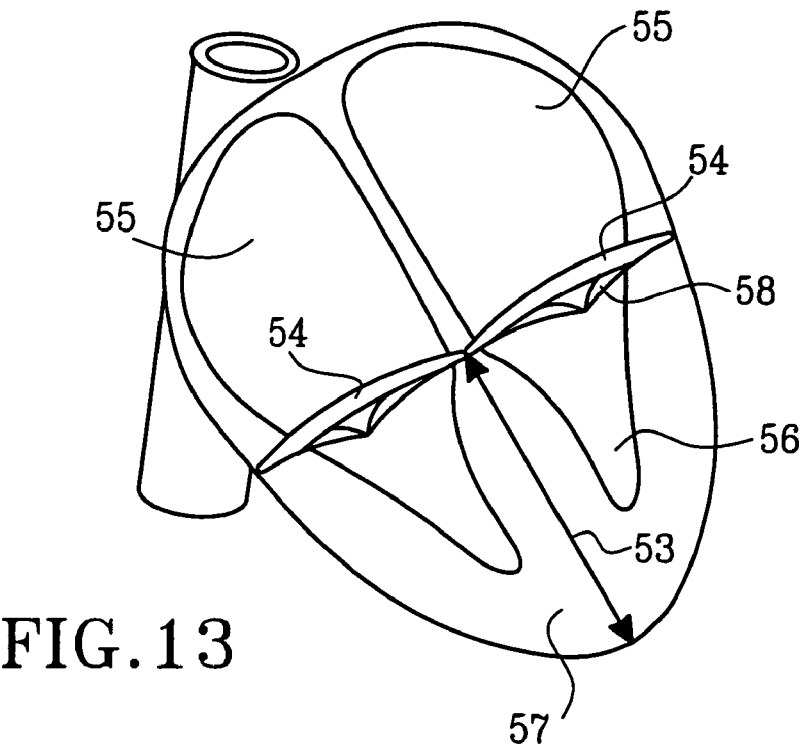
FIG. 13 shows generally an AV-plane of a heart and its function in one position.

From animal experiments one has thus drawn the conclusions that:
- the heart maintains a constant volume during both the diastole and the systole phases;
- the main pumping function of the heart depends on a caudocephaladic movement of the atrioventricular plane (54 in FIG. 13, 14). This movement in turn provides a reciprocal effect of two compartments so that the atriums are filled during the systole phase of the ventricles and that the ventricles are filled at a simultaneous reduction of the volumes of the atriums in diastole phase.
- The atrioventricular plane moves towards the tip of the heart, apex, during systole while the tip of the heart moves inconsiderably during systole and diastole (about 1 mm).

Hoffman and Ritman (1985) carried out a study on dogs and arrived to the fact that the tip of the heart, apex, is maintained rather stable while the atrioventricular plane moves towards apex during systole and towards the atriums during diastole, when the atriums and the ventricles are emptied and filled, alternatively.

Hamilton and Rompf draw their conclusion from animal experiments, but so did also Hoffman and Ritman. But the systolic shortening of the longitudinal axis of the ventricles, i.e., the down going movement of the base of the heart towards apex during systole has been studied on humans using different techniques.

The most extensive studies with regard hereto during the last years have been carried out by Lundbäck (1986). He proved the model of ventricular pumping, the same as previously presented by Hamilton and Rompf, and Hoffman and Ritman, respectively. These studies prove the importance of a longitudinal axis contraction and the systolic movement of the atrioventricular plane towards apex, and that the heart, simultaneously herewith, maintains a constant volume during both diastole and systole, thanks to the heart sac, the pericardium, and the support from surrounding tissues, (Wandt, Birger, Mitral Ring Motion in Assessment of Left Ventricular Function, Linkoping 1998).

Figure 14:
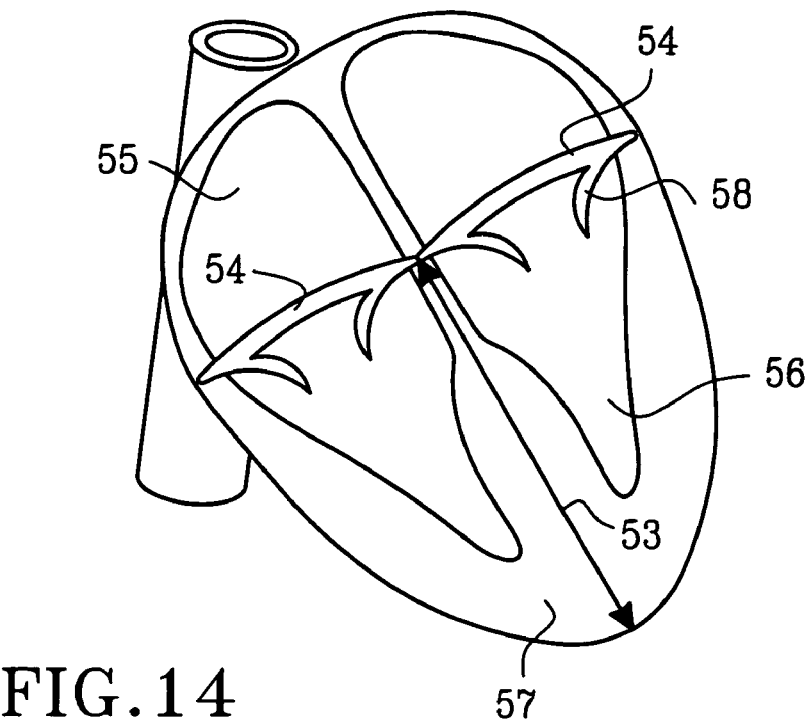
FIG. 14 shows the embodiment of FIG. 13 in a second position.

During early diastole phase, FIG. 14, the atrioventricular plane (the AV-plane) moves with its prosthesis valves in the heart rapidly upward towards the atriums. At the end of the diastole phase the AV-plane moves still more as a result of the contraction which occurs in the atriums. In his study of the left ventricle, Lundbäck has noticed that the left ventricle has an outer diameter of about 68 mm in a healthy young person. In this way the left ventricle contracts during systolic phase in a substantially cylindrical segment having a length of 19 to 22 mm (longitudinally) and having a radius of about 34 mm. The cylindrical segment has a volume of 69 to 80 ml which value corresponds with the normal value of the stroke volume of a healthy young person, i.e., the stroke volume is determined by the longitudinal movement of the AV-plane as well as of its surface in the left ventricle. (Wandt, Birger, Mitral Ring Motion in Assessment of Left Ventricular Function, Linkoping 1998).

The present invention is a heart prosthesis which substantially eliminates or prevents the drawbacks and problems which are connected with prior invented and evaluated heart prosthesis.

Figure 3:
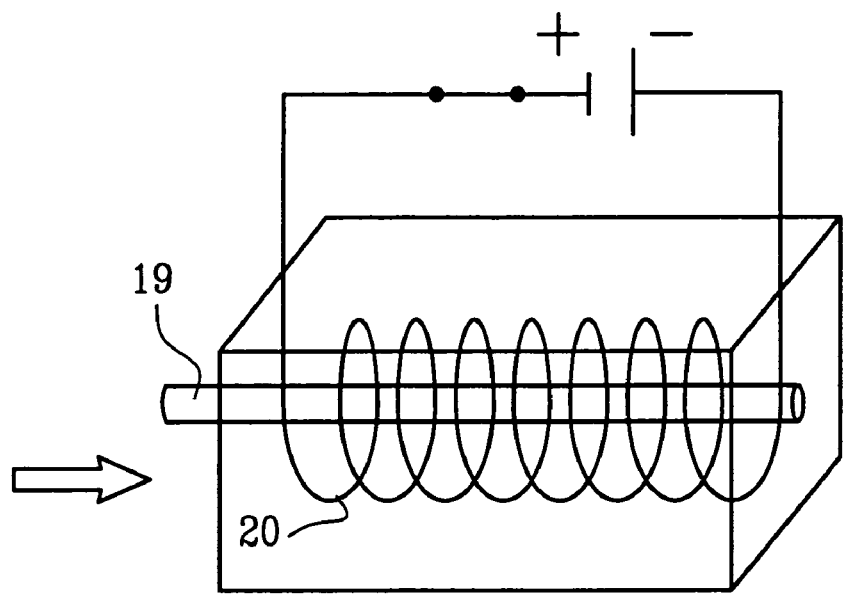
FIG. 3 shows an electromagnet, drawing, used in the present invention in a drawing, activated position.

FIG. 1, 2, 6, 7, 8, 11, 12 show the present invention in its entirety, while FIG. 3, 4, 5, 9, 10, show certain details of an embodiment of the invention, FIG. 13, 14 show, generally an AV-plane in a heart and its function according to Hoffman and Ritman's, Hamilton and Rompf's, and Lundbäck's hypothesis of heart physiology.

The present invention is a completely implantable heart prosthesis which replaces the natural heart, completely or partly. The outer wall 2 of the prosthesis is created of a rigid, or semi-rigid, material, such as a biocompatible polymer and is with regard to size and form about proportional to the natural heart. The outer layer 3 of the walls being in contact with body tissues is constructed of a biocompatible thermoplastic material.

The prosthesis consists of two ventricles each being provided with two openings equipped with artificial valves 4. Through one of the openings blood is pumped out and through the other one blood is received. Further, there are two further compartments, comparable to the natural atriums, whereby the right atrium 5 of the prosthesis is provided with three openings. Off these, is one an opening for outgoing blood to the right ventricle 12 of the prosthesis, and two are inlet openings for blood into the atrium 5. Left atrium 6 comprises however, five openings, of which one is an outlet opening for blood to the left ventricle 13 and the other four are inlet openings through which blood passes from the two lungs to left atrium.

Each compartment of the four described above are provided with their separate activation and controlling device. This device is made of a flexible layer (wall) 7 of an elastic, biocompatible material which is utilized for pumping of blood. This layer 7 is fixed to the respective opening 8. The innermost layer 1 of this first mentioned layer 7 is in direct contact with the flowing blood and is constructed of a hemocompatible material, whereby simultaneously a blood receiving compartment is formed. A free distance 9 is present between the inner side of the outer rigid wall 2 of the prosthesis and the said flexible layer 7.

To summarize, the artificial heart contains four compartments: one corresponding to right atrium 5, one which corresponds to right ventricle 12, one which corresponds to left atrium 6, and one which corresponds to left ventricle 13. In the right atrium of the prosthesis the two vena cava end, vena cava superior 14 and vena cava inferior 15. The rigid outer wall 2 of the prosthesis corresponds to the pericardium of the natural heart, while the flexible, elastic layer 7 surrounding the four compartments corresponds to the natural muscle walls, the myocardium, of the ventricles and the atriums.

From the right atrium 5 of the prosthesis blood flows through a prosthetic valve 4 to the right ventricle of the prosthesis from where it is then pumped to the pulmonary artery (arteria pulmonalis) 16 via the pulmonalisostium of the prosthesis, which is provided with a prosthetic valve.

The oxygenated blood from the lungs flows via the four pulmonary veins (venae pulmonalis) 17 to the left atrium 6 of the prosthesis and then further to the left ventricle 13 of the prosthesis through a prosthetic valve. The elastic layer of the left ventricle of the prosthesis should be 3 to 4 times as thick as the elastic layer of the right ventricle which is due to the higher pressure work at the left side compared to the right side. Left ventricle pumps blood into the large body artery, aorta 18.

The task of the artificial heart is to keep the blood circulating in the body and consists, for that reason, of two pumps connected in series, in the same way as the natural heart, a right and a left pump. The two atriums of the prosthesis serve as reservoirs for the ventricles of the prosthesis and facilitates a rapid filling of these during the filling phase of the prosthesis, diastole. During the ejection phase, systole, the blood is driven with a high speed out into aorta and arteria pulmonalis.

Figure 4:
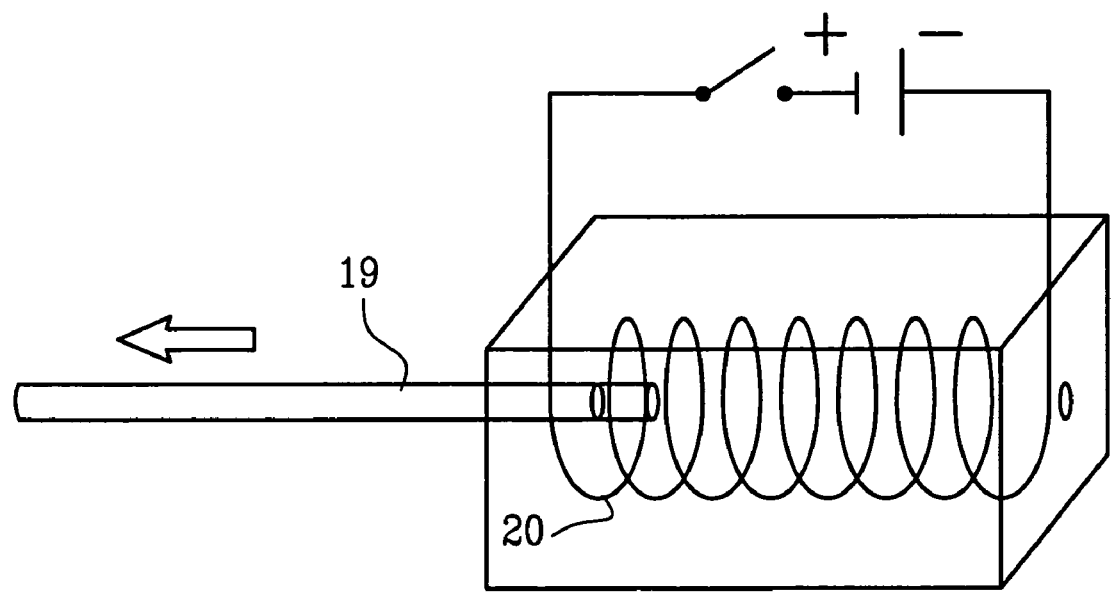
FIG. 4 shows an electromagnet, drawing, in accordance with FIG. 3 in a non-drawing, inactivated position.

Within the hard wall 2 there is a number of mini electromagnets 10 (cf in particular FIGS. 3 and 4). The material of the outer hard wall should then be a suitable thermoplastic material. The movable part of the magnets, the core 11, 19, is present in a fixed contact with the flexible, elastic layer 7. Each magnet 10 contains further a field conduit 20 surrounding the movable metallic core 11, 19.

The electromagnetic system is driven from an electrical source 21. The current can be added in different ways, such as using compact, rechargeable batteries, or via a transformer with a rectifier, which adds a direct current. A smaller electrical conduit running intracutaneous from the inside of the body to its outside is surrounded by a biocompatible material, e.g., Dacron®. Alternatively, the power supply may carried but through transcutaneous transfer of electrical energy through the skin to specific electrodes underneath the skin, in which way the need for using an intra cutaneous running conduit will be eliminated.

The artificial heart functions according to the following.

The function of the artificial heart can be separated into three phases, in the same way as the function of the natural heart, as described above.

Figure 12:
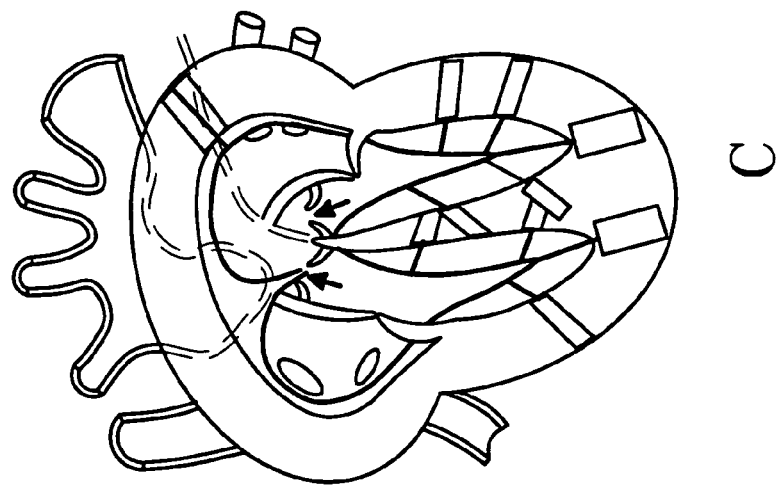
FIG. 12 shows the embodiment according to FIG. 1-2 in diastole phase (A), atrial systole phase (B) and ventricular systole phase (C)
Figure 12:
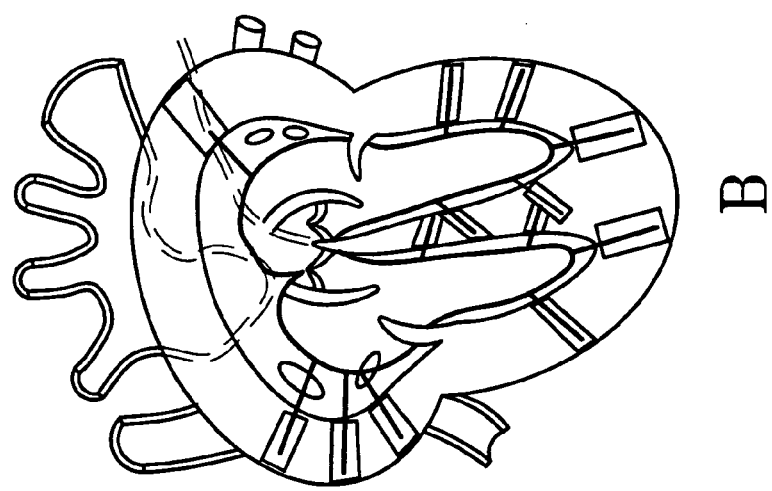
Figure 12:
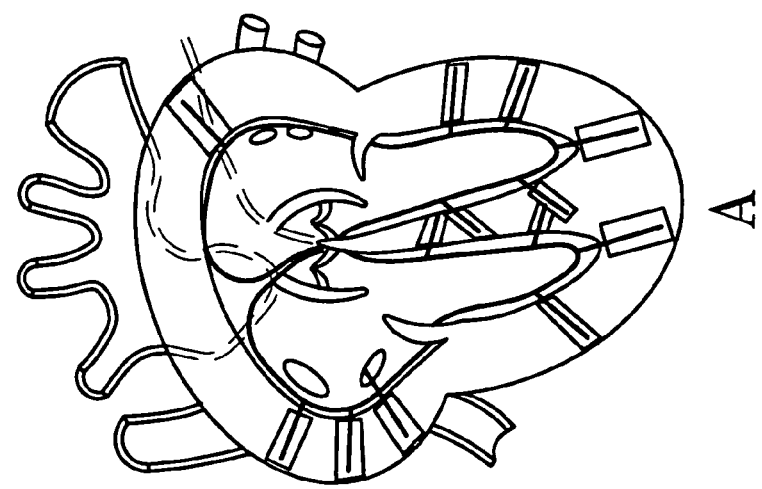

Diastole: During the diastole phase the elastic layer of the respective ventricle is contracted under influence of the electromagnets (drawing magnets) in a direction towards the rigid outer walls (FIG. 12A). Hereby the artificial heart is filled with blood. During the major part of diastole blood flows into the atriums and through the valves between atriums and ventricles.

Atrial systole: During this phase the effect of the electromagnets (drawing magnets) on the elastic layer in the respective atrium (FIG. 12B), whereby the elastic layer is resiliently returned so that remaining amount of blood in the respective atrium is pressed into the ventricles.

Ventricular systole: During this phase the effect of the electromagnets on the elastic layer in the respective ventricle ceases (FIG. 12C). Hereby, the elastic layer returns so that blood is forced out of the ventricles and into the pulmonary artery and aorta. Simultaneously, during this phase the elastic layer in the respective atrium is drawn (FIG. 12C) by means of the electromagnets (drawing magnets) towards their outer rigid wall.

The pressure which is created in the respective ventricle is commonly about 100 to 120 mm Hg on the left side and 15 to 30 mm Hg on the right side. The pressure is separately controlled in the four respective compartments by means of the electromagnets and by means of the thickness of the elastic walls (the thicker the wall, the higher the pressure). The number of electromagnets connected to the respective compartment may also be varied depending on the thickness of the elastic layer and on the drawing-pressing-ability, as desired.

The core of the electromagnets (the movable metallic core) is drawn out of the field conduit by means of the effect of the elastic layer (FIG. 3). A conduit from the electromagnets runs to a digital, electronic circuit board 22, the electronics of which is similar to previously known Acardiac pacing system® in pace-makers, and which regulates the frequency of the electrical impulses to the electromagnetic system in the prosthesis/artificial heart.

Said digital electronic circuit board 22 produces and regulates pulses of electrical current to and through the electromagnets, whereby a magnetic field is created which leads to that the metallic core is drawn into the field conduit (FIG. 4). This in turn leads to that the elastic layer is drawn towards the rigid outer wall.

The digital circuit board 22 receives an input signal from an electrode or sensor 23 which is placed in or adjacent the sinoatrial bundle to receive the natural electrical impulses (one may save that part of the right atrium comprising the sinoatrial bundle at a surgical extraction of the failing heart at the implantation of the prosthesis). Alternatively, one may use a blood pressure sensor 24 placed in the wall of the left arteria carotis communis. This sensor is sensitive to a variation of the blood pressure in arteria carotis communis. In this way the frequency of the impulses derived from the digital electronic circuit board to the electromagnets, is controlled. Thereby, the prosthesis answers to an increase or decrease to the natural, physiological demand of the body.

The circuit board can be programmed so that the electromagnets of the respective atrium and ventricle are separately activated. Furthermore, the size of the current activating the electromagnets of the respective atrium and ventricle can be regulated each individually by providing a desired degree of drawing of the elastic layer towards the rigid outer wall.

Figure 15:
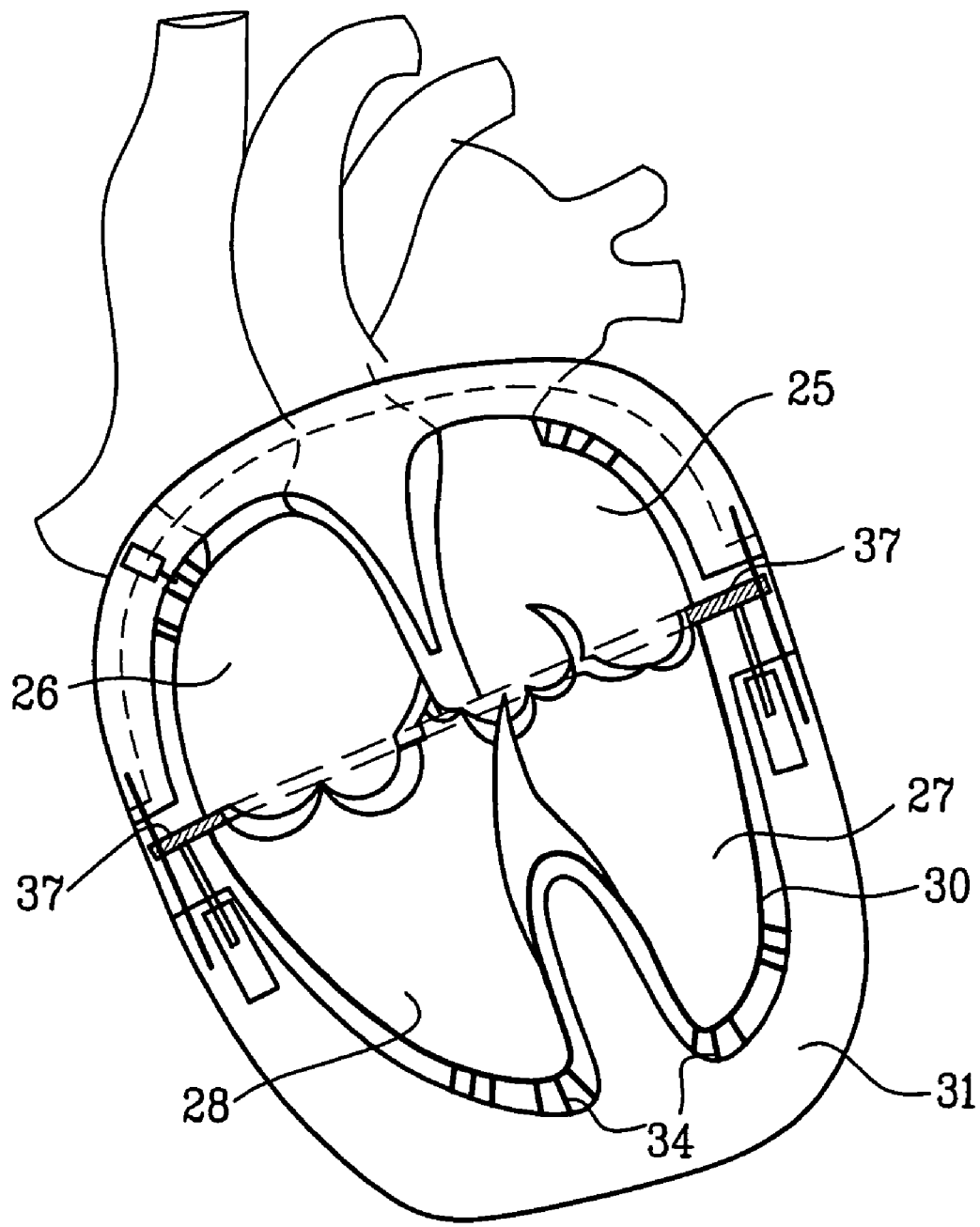
FIG. 15 shows a partial prosthesis where the atrium of the former heart remains.

An alternative embodiment of the present invention is by implanting only one two-compartment unit, e.g., only right and left ventricles. The two ventricles have, in such a case, the same criteria as described above. They are sutured to the natural respective atrium of the patient, whereby the valves between atriums and ventricles are present in the prosthesis part. Hereby, the upper part of the heart prosthesis in such a way that there is only one ingoing opening on each side, one on the right side and one on the left side. The ingoing openings are sewn up with the remaining natural atriums (left and right side). This technique helps in contributing to a faster, easier and safer surgical technology (cf FIG. 15)

Figure 16:
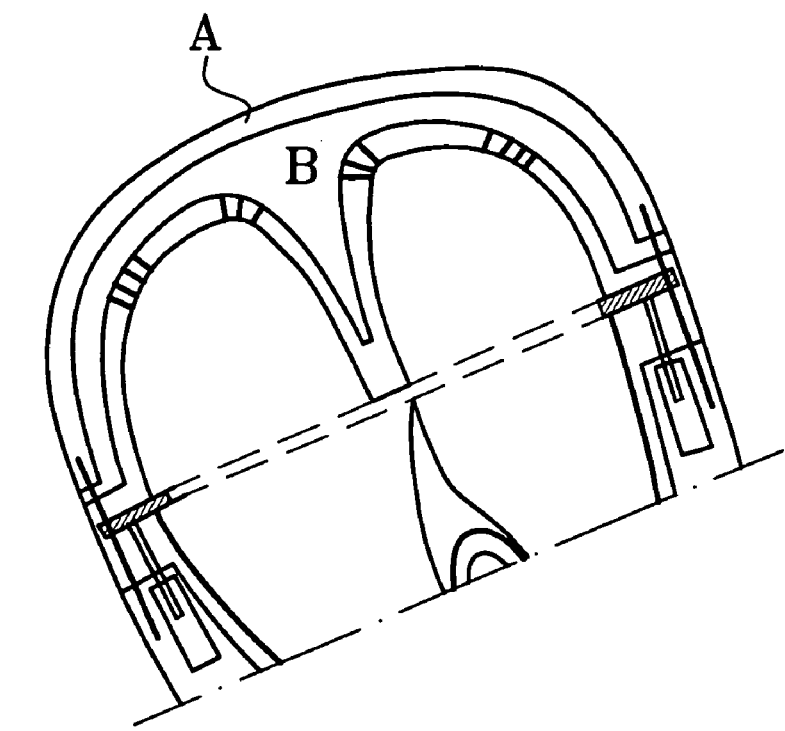
FIG. 16 shows a further embodiment using a divisible prosthesis.
Figure 16:
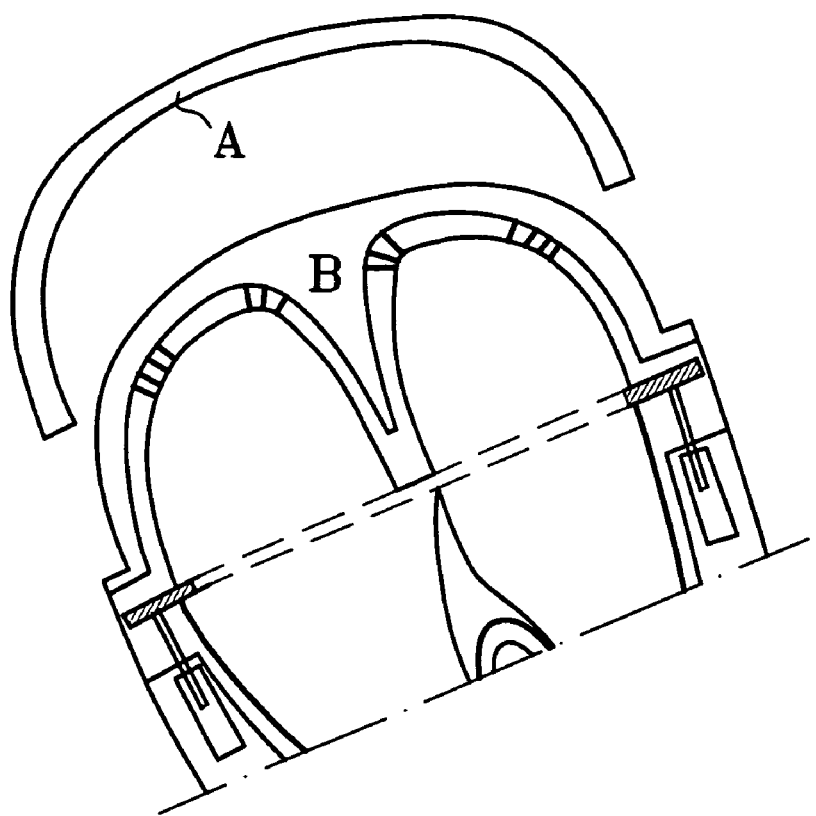

In order to further improve the prosthesis the upper outer walls of the atriums can be constructed in such a way that it consists of two, almost identical parts, which together forms the outer rigid wall of the atriums (cf FIG. 16). Herein the parts have been denoted A and B. Part A is sewn up with the natural atrium and part B will be in a fixed relation to the remaining part of the pump/prosthesis. This technique facilitates optional future reoperations, if one should need to replace the whole or part of the prosthesis. One can replace damaged parts or the parts one count on should need to be replaced after a certain time period, without need for removing part A, which is fixedly connected to the atrium. The only thing one needs to do is to screw loose part B from part A and remove the prosthesis including part B.

Figure 17:
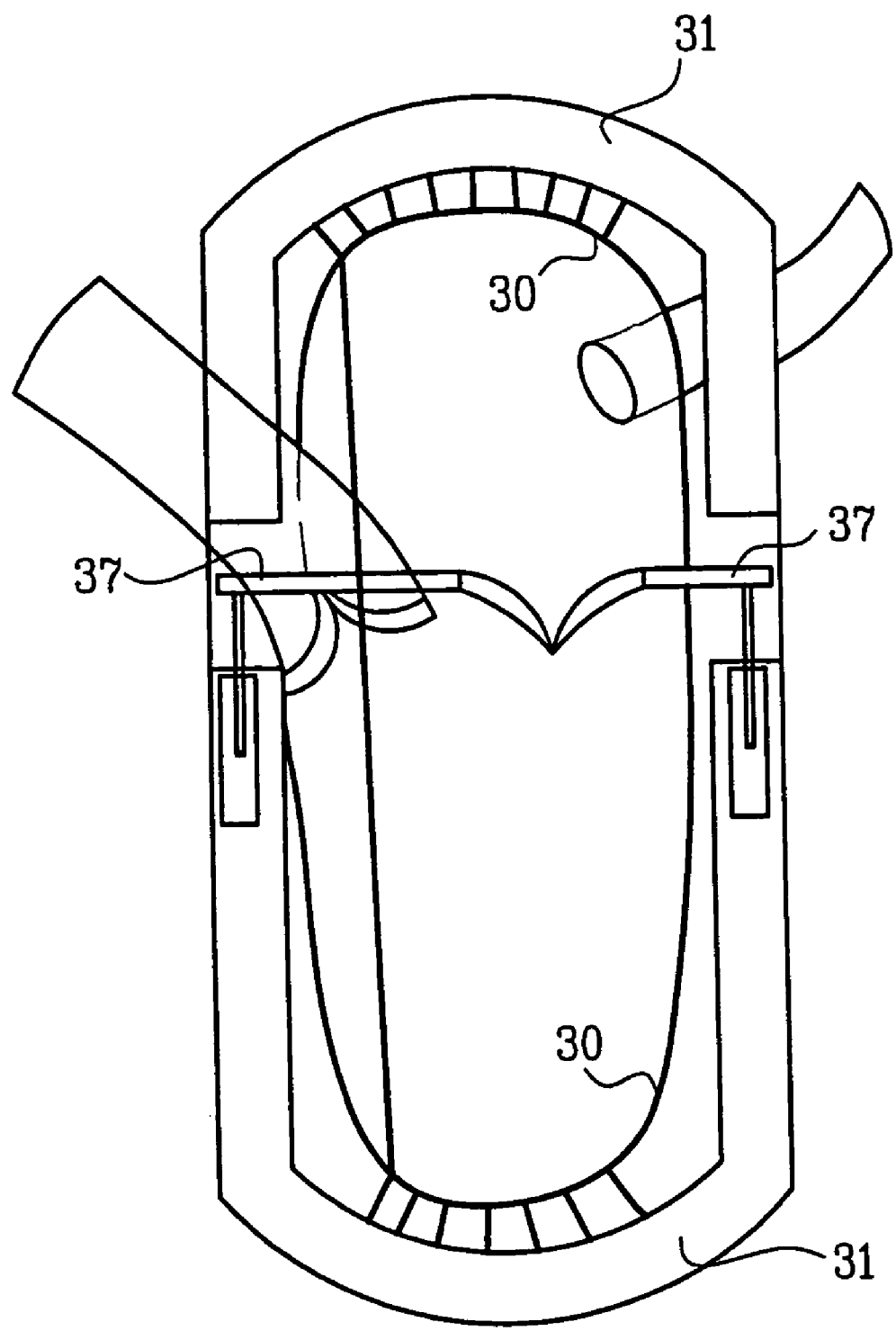
FIG. 17 shows a further embodiment of a partial prosthesis.

In accordance with another embodiment half of, or only a quarter of a heart be replaced using a prosthesis according to the present invention. Such a half prosthesis is shown in FIG. 17. Two such half prosthesis may also form a total prosthesis.

Figure 6:
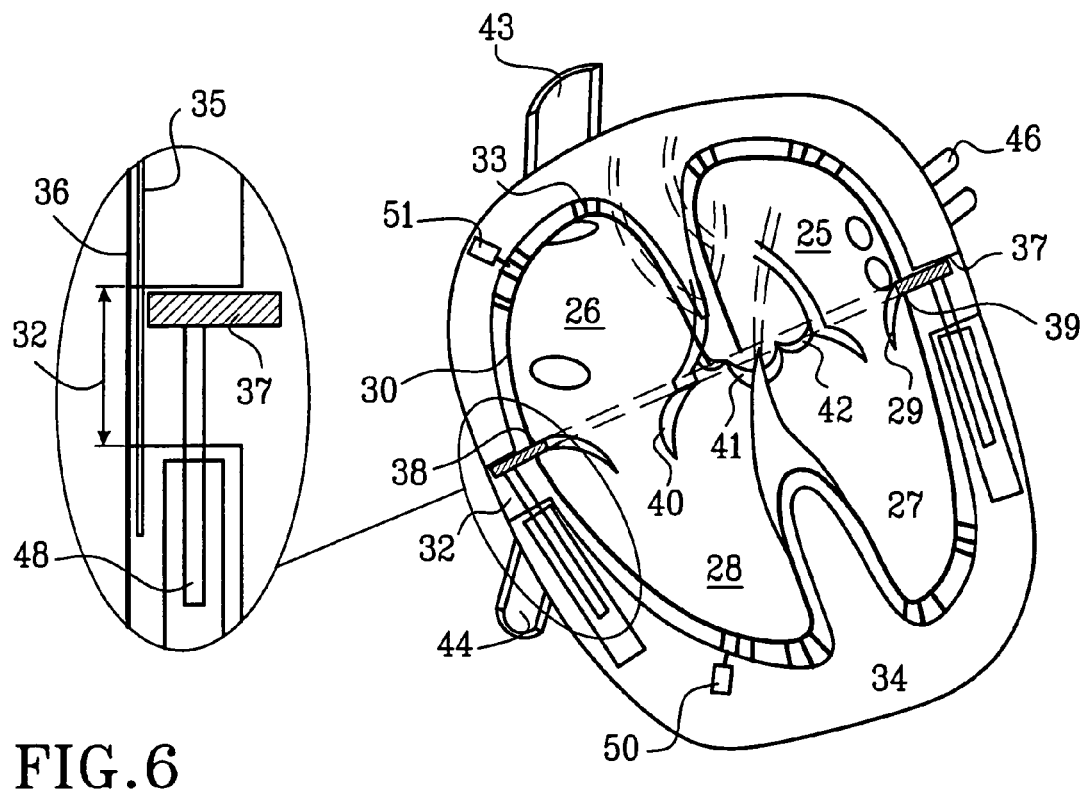
FIG. 6 shows a second embodiment of the invention comprising a further whole prosthesis in a diastole phase.
Figure 7:
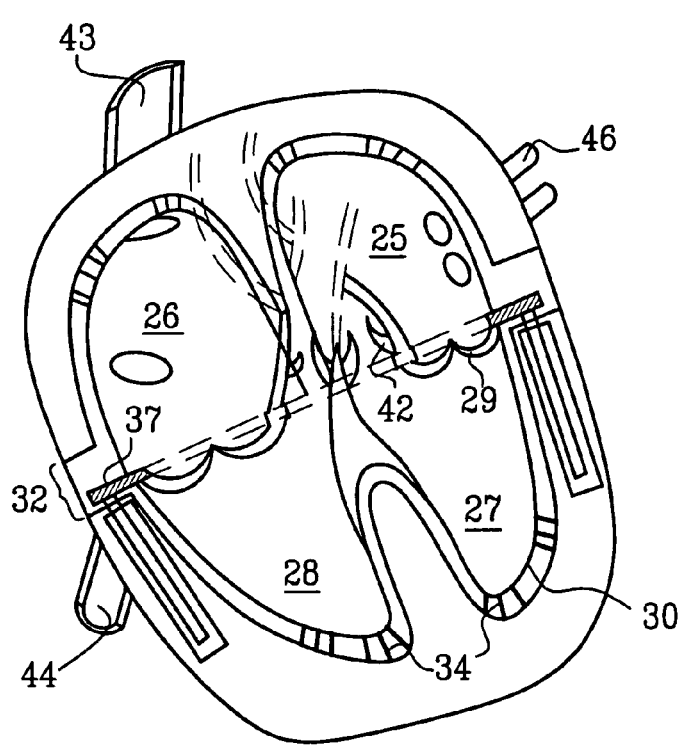
FIG. 7 shows the embodiment of FIG. 6 in a systole phase.

A further embodiment of the invention is shown in FIGS. 6 and 7, which embodiment also is a completely implantable prosthesis, whereby it consists of two halves (right and left) where each half is divided into two compartments, corresponding to an atrium 25, 26 and one ventricle 27, 28. These compartments are connected with each other via a valve prosthesis 29, 40. The walls of the atriums and ventricles consist, as described above, of an elastic, flexible layer 30. Furthermore, there is an outer rigid wall 31, such as in the previously described embodiment, but contrary to that there is a slit 32 between the outer walls of the ventricles and the outer walls of the atriums. This slit is 10 to 20 mm. The walls of the atriums, the elastic wall, is fixed at the base of this prosthesis to the outer walls 33 of the atriums, simultaneously as the elastic walls of the ventricles are fixed to the outer walls of the ventricles in the apex of the prosthesis or its tip (lower end) 34.

Further there are a number of metal pins 35 having a diameter of one to some millimeters and having a length of 3 to 4 cm arranged to hold the outer walls of the atriums and the outer walls of the ventricles in fixed relation to each other. A thin layer 36 of the outer rigid wall covers the slit described on the outside of the prosthesis.

Further, there is a metallic plate 37 which corresponds to the atrioventricular plane 54 of the natural heart (FIG. 13, 14), which plate has a thickness of one to some millimeters and separates the atriums 25, 26 from the ventricles 27, 28. The elastic wall layer of the atriums is fixedly arranged to the upper side 38 of the metal plate 37 and the elastic wall layer of the ventricles is fixedly arranged to the lower side of the metal plate 37. The metal plate 37 can be exchanged to any other suitable material, which fulfills the demands of being long term lasting and feasibly non-elastic or flexible.

Figure 8:
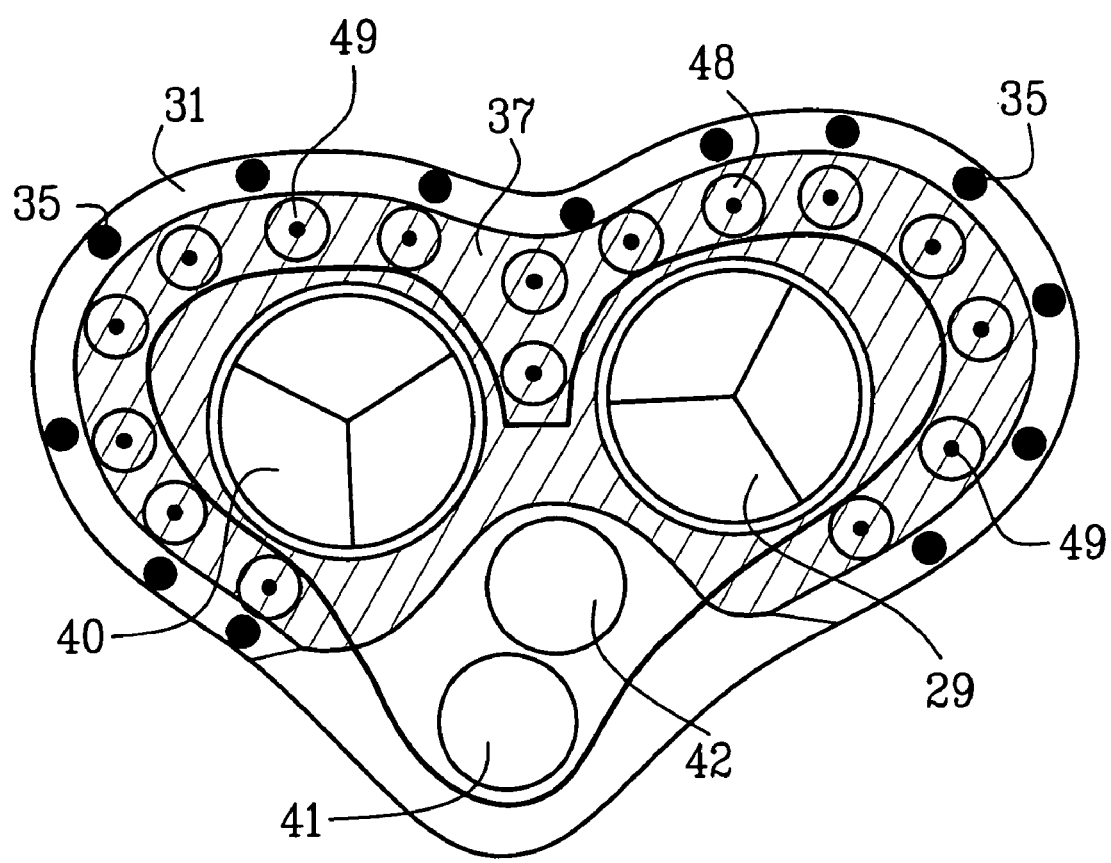
FIG. 8 shows the embodiment of FIGS. 6 and 7 in a cross-section.

In the metal plate 37 there are two openings connecting the atriums 25, 26 of the prosthesis with the ventricles 27, 28 of the prosthesis with each other, one in each side. The openings correspond to the litralis valve 29 and the tricuspidalis valve 40 and are each provided with valve prostheses. Simultaneously, each ventricle has an outlet opening which is provided with valve prostheses and which correspond to pulmonalis valve 41 on the right side, and the aorta valve 42 on the left side and which are arranged outside the metal plate 37 (FIG. 8).

In the same way as in the above described embodiment this embodiment comprises four compartments: one 26 corresponding to the right atrium, one 28 corresponding to the right ventricle, one 25 corresponding to the left atrium and one 27 corresponding to the left ventricle. In the right atrium 26 of the prosthesis the two vena cavas end, vena cava superior 43 and vena cava inferior 44.

From the right atrium 26 blood flows through the valve prosthesis 40 to the right ventricle 28 of the prosthesis from where it is then, via the pulmonalisostium of the prosthesis being provided with a valve prosthesis 41 is pumped to the pulmonary artery (arteria pulmonalis) 45.

The oxygenated blood from the lungs flows via the four pulmonary veins (venae pulmonalis) 46 to the left atrium of the prosthesis and then further to the left ventricle 27 of the prosthesis through a valve prosthesis 29. The elastic layer of the left ventricle of the prosthesis should be 3-4 times thicker than that of the right ventricle, which is due to the larger pressure work carried out on the left side compared to the right side. Left ventricle pumps blood into the large body artery, aorta 47.

The task of the artificial heart is to keep blood circulating in the body and consists, for that reason, of two pumps connected in series, in the same way as the natural heart, one right and one left pump. The two atriums of the prosthesis serve as reservoirs for the ventricles of the prosthesis and facilitates a rapid filling of these during the filling phase, diastole, of the prosthesis. During the ejection phase, systole, the blood is driven with a high speed out into aorta and arteria pulmonalis.

The outer rigid wall 31 of the prosthesis, in which the metal plate 37 of the prosthesis moves to and fro, corresponds to the surrounding sac, the pericardium, of the natural heart. In the same way the elastic wall 30 of the prosthesis corresponds to the muscle wall, the myocardium, of the natural wall. As described above, the to and fro going movement of the metal plate within the slit 32 of the outer rigid wall of the prosthesis is similar to the movement of the AV-plane of the natural heart according to the models of Hamilton and Rompf (1932), Hoffman and Ritman (1985) and Lundbäck (1986).

Figure 9:
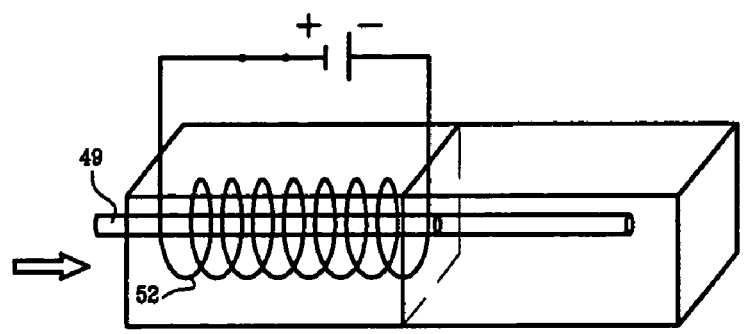
FIG. 9 shows a second electromagnet, pressing, used in the second embodiment of the present invention according to FIG. 6 in an inactivated position.

Unlike the first described embodiment, this embodiment shows some electromagnets 48 (FIGS. 9 and 10) having an opposite function (pressing magnets) which are arranged to the upper edge (FIG. 8) in the outer wall of the ventricles. The movable core 49 of the electromagnets are fixed to the underside 39 of the metal plate. Further, there is a number of electromagnets 50 (FIGS. 3 and 4) within each outer wall of the ventricles. The movable parts of these electromagnets (drawing magnets) are present and fixed to the outside of the elastic wall layer 30 of the ventricles.

In stead of pressing magnets placed outside of the ventricles in the rigid wall, drawing magnets can be placed outside the atriums in the upper edge of the rigid wall. Even combinations of drawing and pressing electromagnets can be present.

Further, there is a number of electromagnets 51 (drawing) in the outer wall of each atrium, the cores of which are fixedly arranged to the elastic wall layer 30 of the atriums.

The material of the outer wall 31 of the heart prosthesis should, as mentioned above, be made of a suitable, biocompatible thermo plastic material. Further, the elastic wall should as such or in a laminate has an Ahemokompatibel® surface directed to the respective compartment, which surface will be brought into contact with blood.

Figure 5:
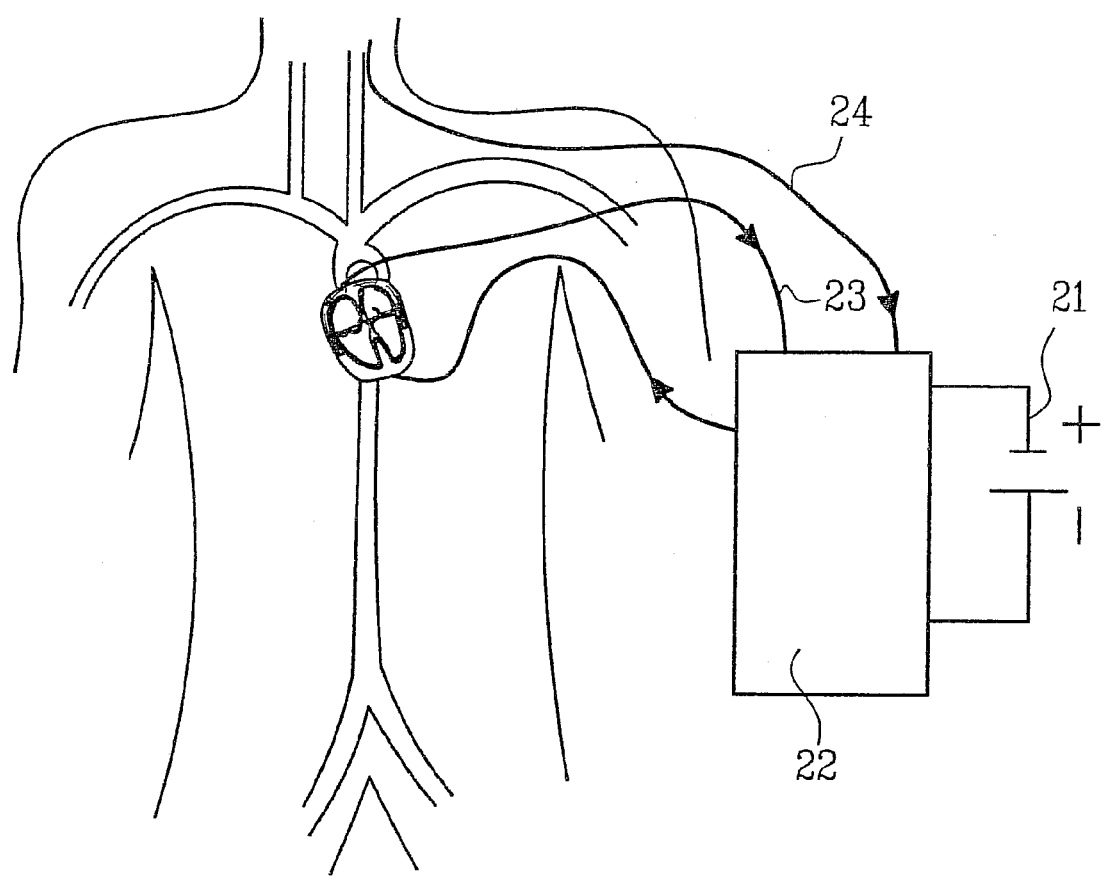
FIG. 5 shows an implanted heart prosthesis according to the invention with a control unit.
Figure 10:
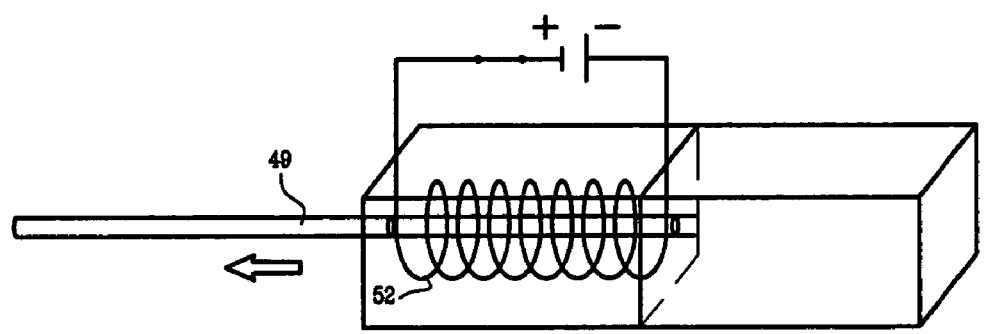
FIG. 10 shows the electromagnet according to claim 9 in a pressing, activated position.

Each electromagnet of the type pressing magnet comprises a field conduit 52 surrounding the core 49. When the electromagnets are arranged as pressing magnets the core is pressed into the field conduit by means metal plate by means the effect of the thick, elastic wall layer 30 of the ventricles (FIG. 9), whereby they are passed out of the field conduit when current is allowed to pass through this (FIG. 10). A conduit from the electromagnets runs to a digital, electronic board 22, which corresponds to the board 22, FIG. 5, of the embodiment first described.

The prostheses can be driven in the same way as the first described embodiment.

Figure 11:
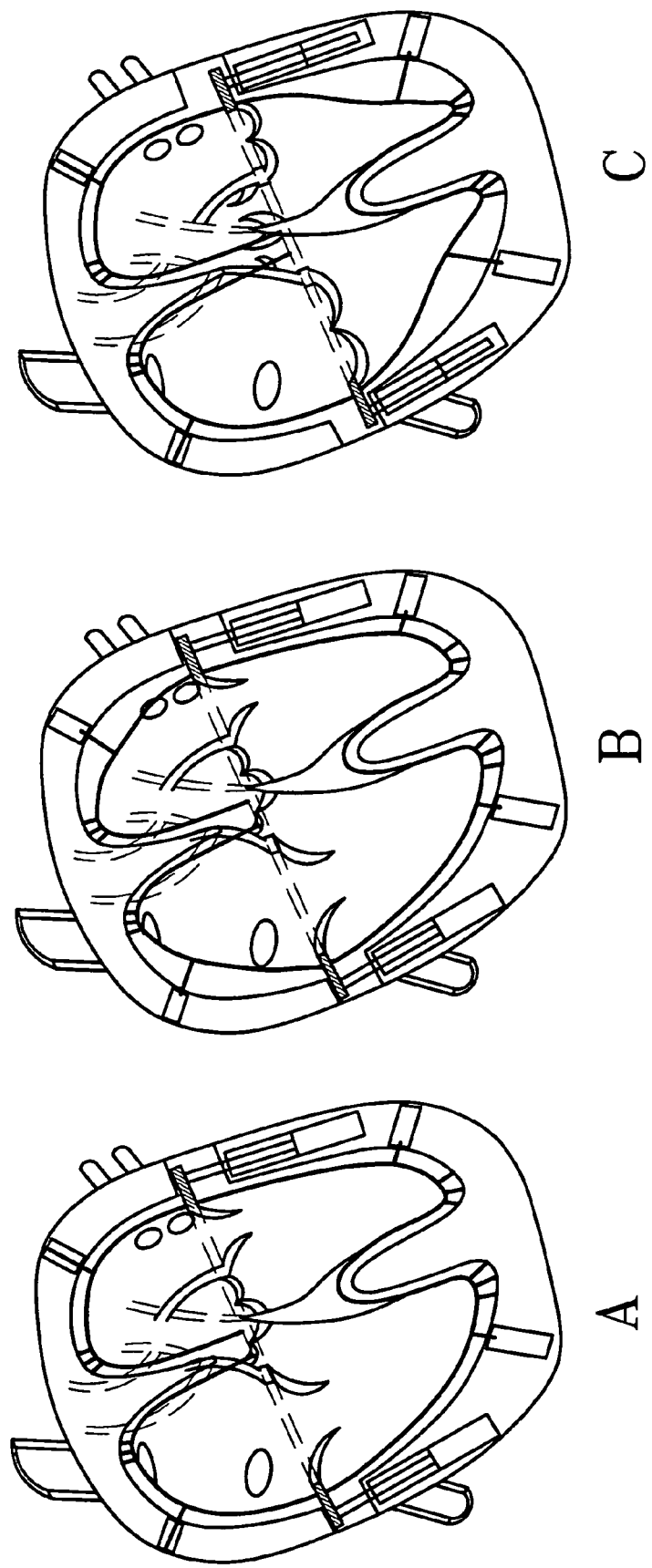
FIG. 11 shows the embodiment of FIG. 6-8 in diastole phase (A), atrial systole phase (B) and ventricular systole phase (C)

This further embodiment functions as follows:

Diastole: In the beginning of diastole (FIG. 11A) the metal plate is drawn up towards the lower edge of the outer wall of the atrium of the prosthesis by means of electromagnets (pressing) 48 and the elastic wall of the respective ventricle is drawn towards its hard rigid wall by means of the electromagnet 50 (drawing). During the first third part to the first half of the diastole phase of the prosthesis the filling of the ventricle is done very fast due to the blood collected in the atriums during the previous systole phase of the ventricles, and which is now pressed to the respective ventricle through valve prostheses, which correspond to the mitralis 29 and tricuspidalis 40 valves, when the metal plate 37 is pushed upward towards the atriums by means of the magnetic force. Simultaneously, there is a reduction of the volumes of the atriums of the prosthesis, as the heart maintains a constant volume during both diastole and systole phases (acc. to Hoffman & Ritman, Hamilton et al, Lundbäck a. o.). Alternatively the metal plate 37 of the prosthesis can be pressed upward towards the atriums of the prosthesis in the beginning of the diastole phase by means of a hydraulic device being activated by means of an implanted mini hydraulic engine.

During the second third of the diastole a minor amount of blood is moved directly from the veins through the atriums to the ventricles.

Atrium systole: During the first phase (FIG. 11B) the drawing effect of the electromagnets 51 on the elastic wall layers of the respective atriums ceases, whereby the elastic wall layers return to a basic position, whereby the remaining part of the blood of the respective atrium is pressed into the respective ventricle.

Ventricle systole: During this phase (FIG. 11C) the effect of the electromagnets 50 in the outer rigid wall of the ventricles, ceases, whereby the elastic layer retains its basic position and the metal plate 37 is drawn to the ventricles (the apex of the prosthesis) by means of the effect by the thick elastic inner wall layers of the ventricles, and after ceased pressure influence of the pressing magnets 48. The inner wall layer hereby is resiliently returned and the blood is pressed out through the pulmonary artery 45 and aorta 47, when the valve prosthesis corresponding to the mitralis and tricupidalis valves have been closed. When the atrium systole phase of the atrium is finished the elastic wall layer of the atriums is drawn towards the outer hard rigid walls by means of the electromagnets 51 present in the outer rigid walls of the atriums, whereby the pressure decreases in the respective atrium and the blood flows into the respective atrium of the prosthesis from the veins, vena cava superior, and vena cava inferior, and the pulmonary vein, venae pulmonalis.

The pressure being created in the respective ventricle is commonly 100 to 140 mm Hg on the left side and 15 to 30 mm Hg on the right side. The pressure is controlled separately in the four respective compartments depending on the thickness of the elastic walls, which can be the same or not in the different respective compartments (the greater thickness, the larger pressure).

The invention claimed is:

1. A heart prosthesis intended to be implanted in a patient to replace the pumping activity of a heart comprising at least two compartments, substantially surrounded by a house with a rigid wall and containing a number of drawing and/or pressing devices, which are partly fixedly attached to said rigid-wall provided house and partly fixedly attached to a flexible, elastic wall layer arranged in a respective compartment, whereby the drawing and/or pressing devices are arranged to draw said elastic wall layer towards said rigid-wall provided house for filling said compartments, the prosthesis also comprising two halves, comprising an atrium, and ventricles, respectively, separated by a plate with at least one valve, which plate is arranged to be able to be moved between the ventricles and atriums by means of drawing and/or pressing devices arranged in said rigid wall provided house.

2. A heart prosthesis according to claim 1, wherein the heart prosthesis comprises four compartments.

3. A heart prosthesis according to claim 1, wherein the drawing and/or pressing devices are drawing and pressing electromechanical devices, respectively, including electromagnets.

4. A heart prosthesis according to claim 1, wherein said plate is arranged to be moved by means of electromagnets or a hydraulic device arranged in said wall.

5. A heart prosthesis according to claim 1, wherein the drawing and/or pressing devices are drawing, and pressing, respectively, hydraulically activated pistons.

6. A heart prosthesis according to claim 1, wherein the heart prosthesis is arranged to be controlled digitally via software present in a circuit board for diastole, atrial systole, and systole.

7. A heart prosthesis according to claim 1, wherein the heart prosthesis is supplied with energy from one or more DC batteries.

* * * * *